United States Patent
Han et al.

(10) Patent No.: US 11,059,875 B2
(45) Date of Patent: Jul. 13, 2021

(54) COMPOSITION FOR PREVENTING OR TREATING CARDIOFACIOCUTANEOUS SYNDROME

(71) Applicant: Korea Advanced Institute of Science and Technology, Daejeon (KR)

(72) Inventors: Yong Mahn Han, Daejeon (KR); Jung Yun Choi, Daejeon (KR); Bum Soo Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 43 days.

(21) Appl. No.: 16/269,984

(22) Filed: Feb. 7, 2019

(65) Prior Publication Data
US 2019/0241635 A1 Aug. 8, 2019

(30) Foreign Application Priority Data
Feb. 8, 2018 (KR) .................. 10-2018-0015574

(51) Int. Cl.
| | |
|---|---|
| *C07K 14/51* | (2006.01) |
| *A61K 31/7088* | (2006.01) |
| *A61K 31/5377* | (2006.01) |
| *A61K 31/4439* | (2006.01) |
| *A61K 31/4709* | (2006.01) |
| *A61K 31/519* | (2006.01) |
| *A61P 9/00* | (2006.01) |
| *C12Q 1/02* | (2006.01) |
| *G01N 33/50* | (2006.01) |

(52) U.S. Cl.
CPC .......... *C07K 14/51* (2013.01); *A61K 31/4439* (2013.01); *A61K 31/4709* (2013.01); *A61K 31/519* (2013.01); *A61K 31/5377* (2013.01); *A61K 31/7088* (2013.01); *A61P 9/00* (2018.01); *C12Q 1/025* (2013.01); *G01N 33/5044* (2013.01); *G01N 2800/385* (2013.01)

(58) Field of Classification Search
CPC ............... C07K 14/51; G01N 33/5044; G01N 2800/385; A61K 31/519; A61K 31/5377; A61K 31/4439; A61K 31/4709; A61K 31/4725; A61K 38/1875; A61P 9/00; A61P 19/00; A23V 2200/306
See application file for complete search history.

(56) References Cited

PUBLICATIONS

Cardiofaciocutaneous Syndrome (at https://www.cincinnatichildrens.org/health/c/cardiofaciocutaneous-syndrome) (retrieved from the internet Nov. 4, 2020) (Year: 2020).*
Galunisertib Clinical trial (Clinical Trials.gov, NCT02008318; posted Dec. 11, 2013; Sponsor; Eli Lilly and Company), at https://clinicaltrials.gov/ct2/show/ results/NCT02008318 (2013). (retrieved from the internet Nov. 5, 2020) (Year: 2013).*

(Continued)

*Primary Examiner* — Dennis Heyer
(74) *Attorney, Agent, or Firm* — Cesari & McKenna, LLP

(57) ABSTRACT

The present invention relates to a pharmaceutical composition for the prevention or treatment of CFC (cardiofaciocutaneous) syndrome comprising a TGF-β signaling pathway inhibitor or a BMP signaling pathway activator. The treatment of SB-431542 or BMP4 protein was confirmed to increase the ALP activity and bone mineral deposition in the osteoblasts originated from the induced pluripotent stem cells derived from CFC syndrome patients. Thus, the TGF-β signaling pathway inhibitor containing SB-431542 or the BMP signaling pathway activator containing BMP4 protein can be effectively used for the prevention or treatment of CFC syndrome.

3 Claims, 15 Drawing Sheets
(14 of 15 Drawing Sheet(s) Filed in Color)
Specification includes a Sequence Listing.

(56) References Cited

PUBLICATIONS

Han et al. in Stem Cells 33:1447-1455 (2015) (Year: 2015).*
Wrighton et al. in The Journal of Molecular Biology 284(15), 9755-9763 (2009) (Year: 2009).*
Abe et al "Prevalence and Clinical Features of Costello Syndrome and Cardio-Facio-Cutaneous Syndrome in Japan: Findings from a Nationwide Epidemiological Survey" American Journal of Medical Genetics Part A vol. 158A, pp. 1083-1094, 2012.
Aoki et al "The RAS/MAPK Syndromes: Novel Roles of the RAS Pathway in Human Genetic Disorders" Human Mutation vol. 29, pp. 992-1006, 2008.
Carvajal-Vergara et al "Patient-Specific Induced Pluripotent Stem Cell Derived Models of LEOPARD Syndrome" Nature vol. 465, pp. 808-812, 2010.
Huebsch et al "Miniaturized iPS-Cell-Derived Cardiac Muscles for Physiologically Relevant Drug Response Analyses" Scientific Reports vol. 6, pp. 1-12, 2016.
Inoue et al "New BRAF Knockin Mice Provide a Pathogenetic Mechanism of Development Defects and a Therapeutic Approach in Cardio-Facio-Cutaneous Syndrome" Human Molecular Genetics vol. 2014, pp. 1-14, 2014.
Moriya et al "Adult Mice Expressing a BRAF Q241 R Mutation on an ICR/CD-1 Background Exhibit a Cardio-Facio-Cutaneous Syndrome Phenotype" Human Molecular Genetics vol. 24, pp. 7349-7360, 2015.
Niihori et al "Gremline KRAS and BRAF Mutations in Cardio-Facio-Cutaneous Syndrome" Nature Genetics vol. 38, pp. 294-296, 2006.
Rodriguez-Viciana et al "Germline Mutations in Genes Within the MAPK Pathway Cause Cardio-Facio-Cutaneous Syndrome" Science vol. 311, pp. 1287-1290, 2006.

* cited by examiner

[Figure 1]
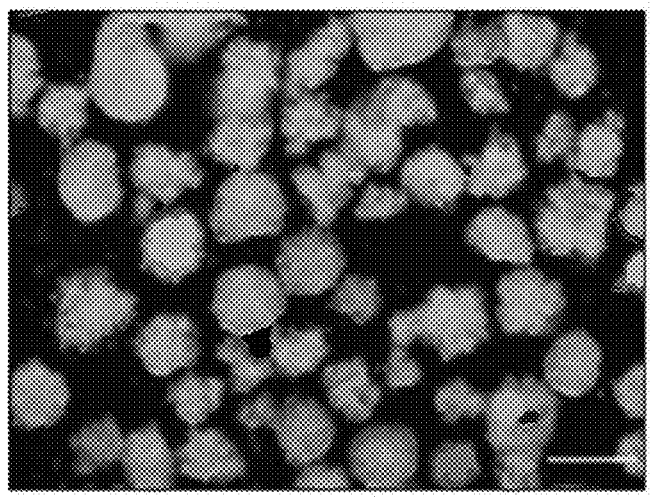
WT
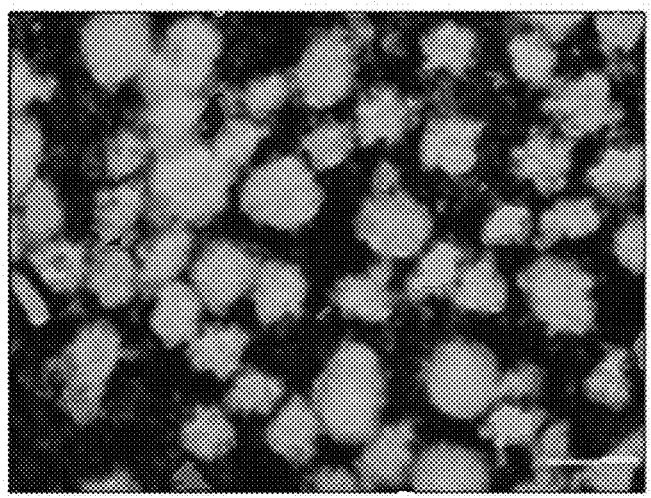
CFC2
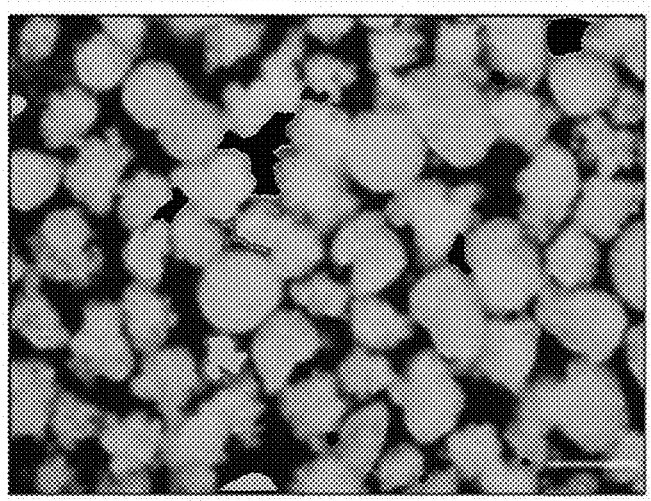
CFC7

[Figure 2]
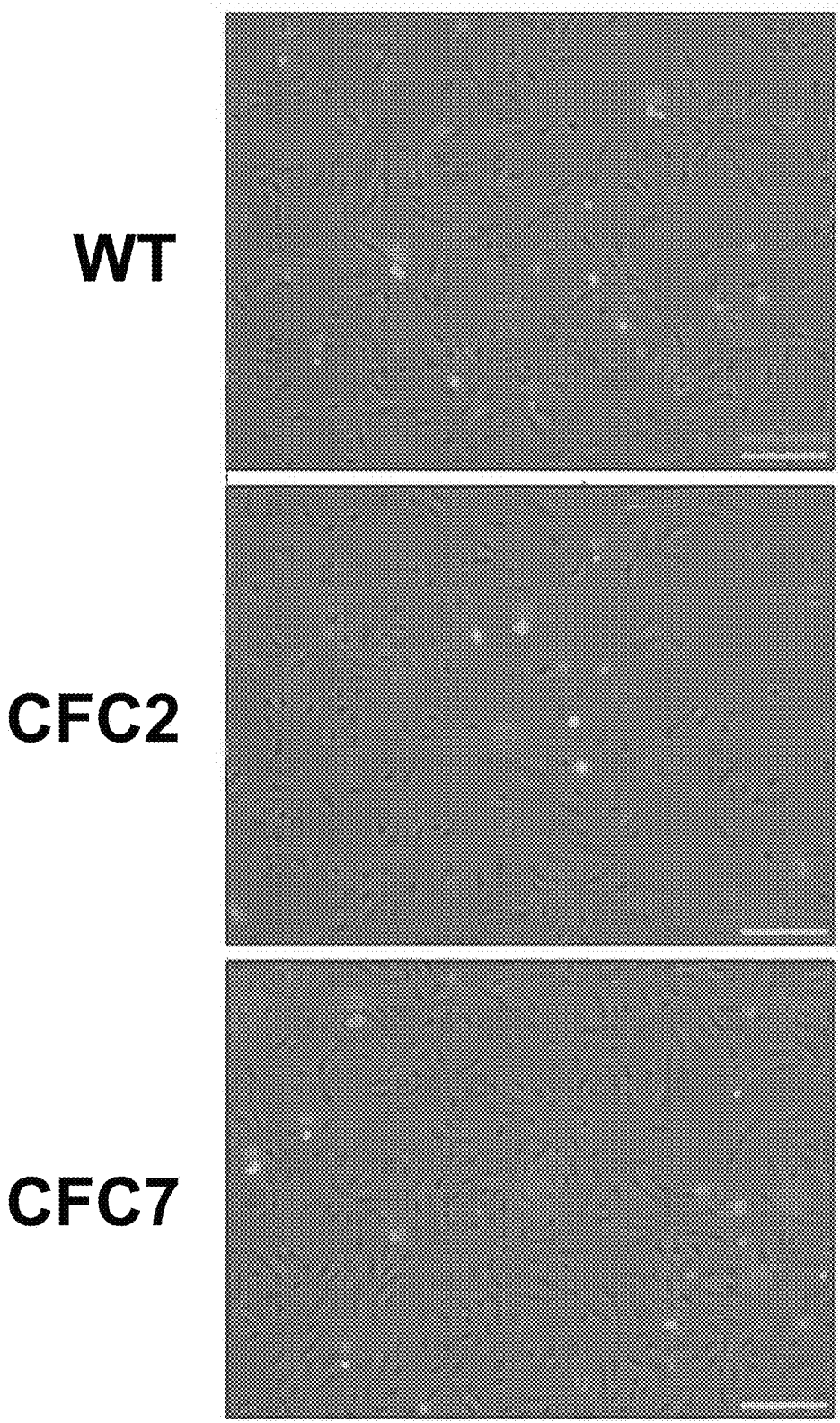

[Figure 3]
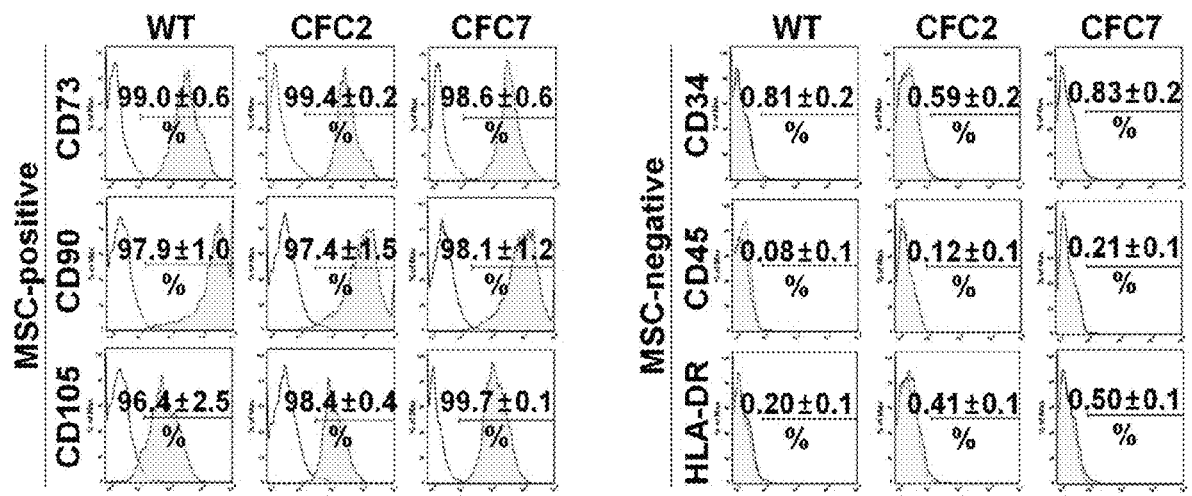

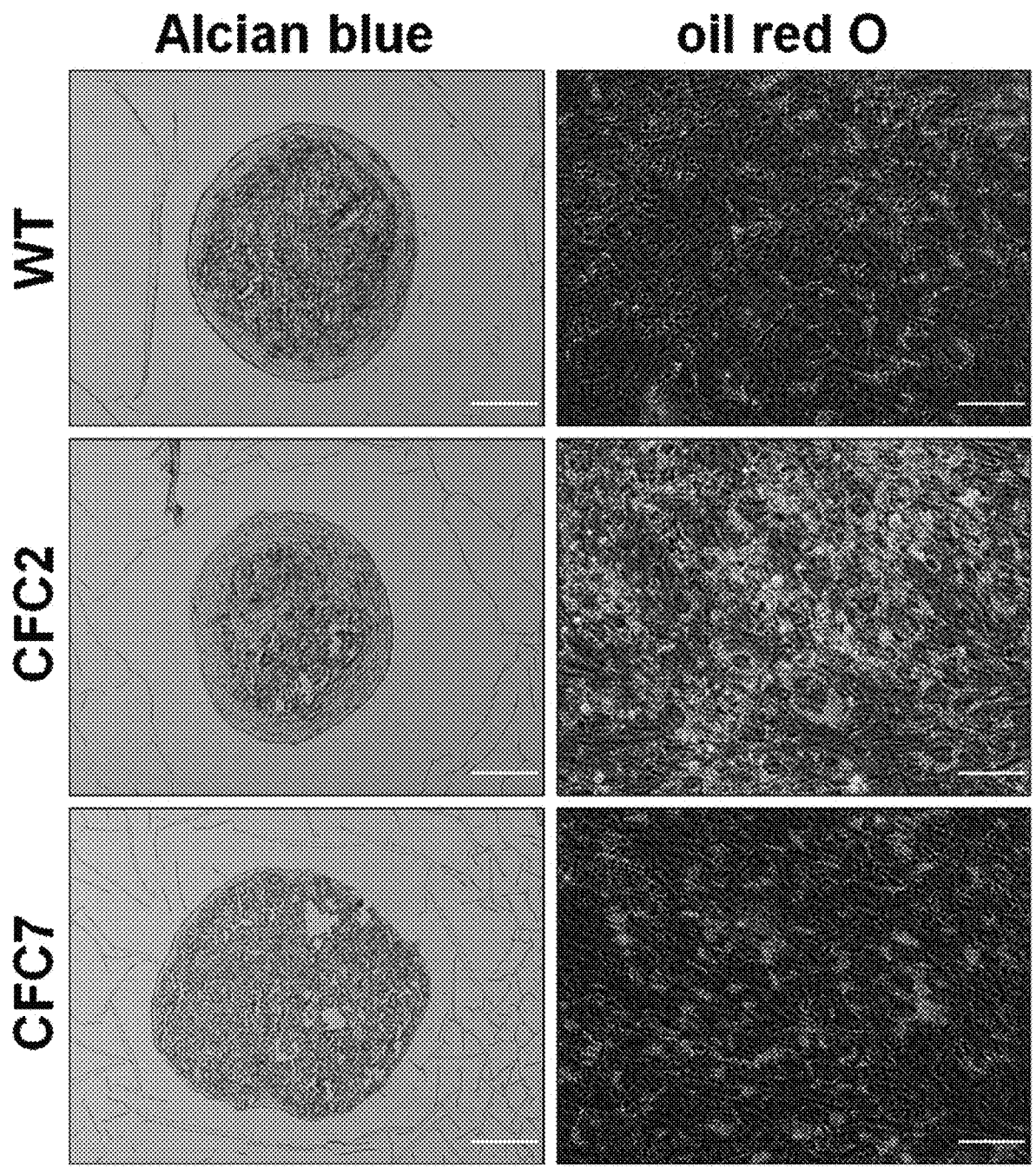
[Figure 4]

[Figure 5]
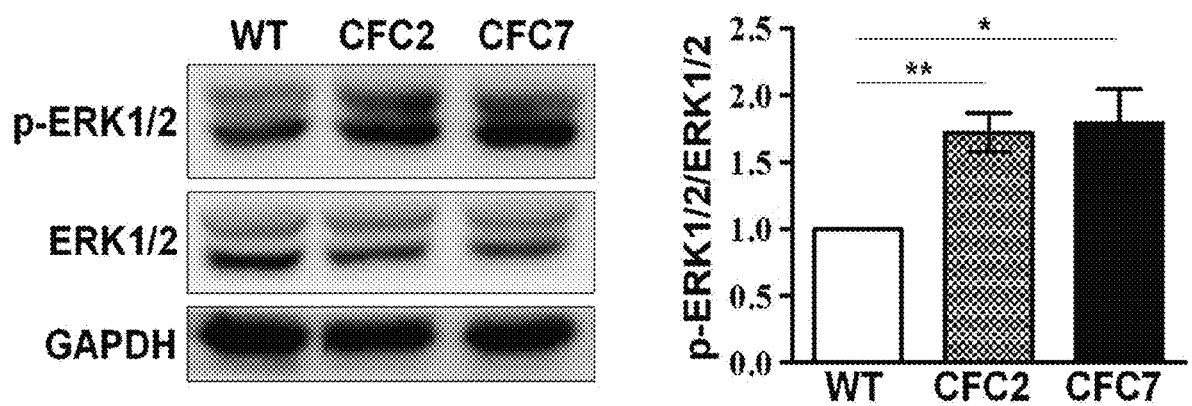

[Figure 6]
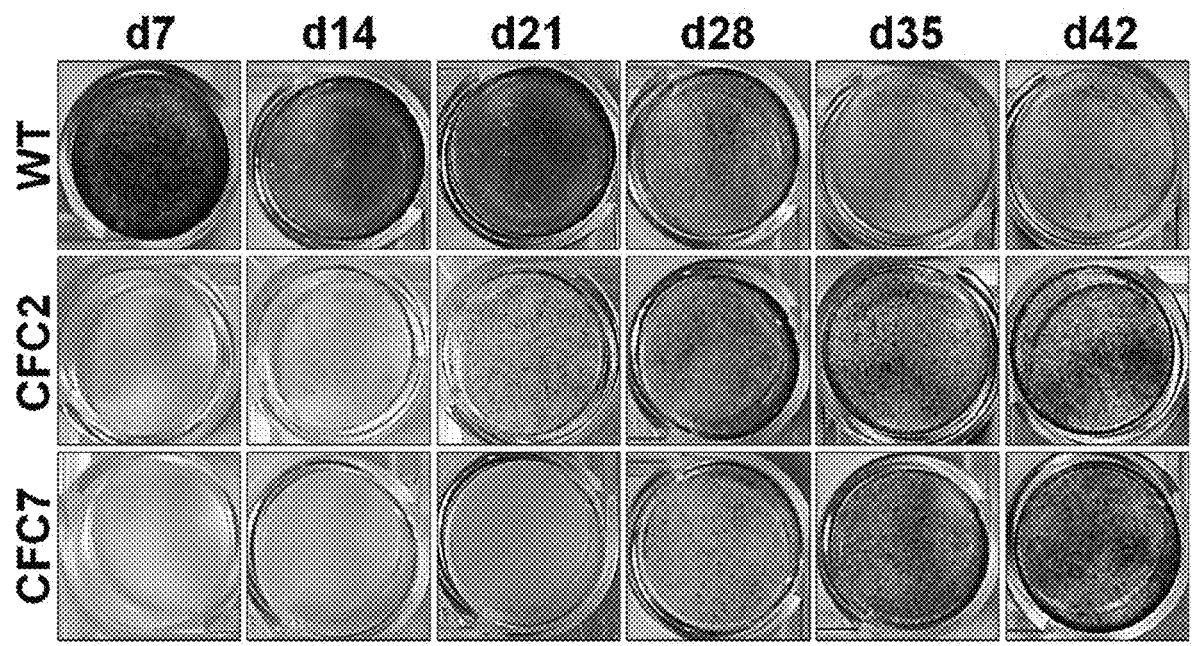

[Figure 7]
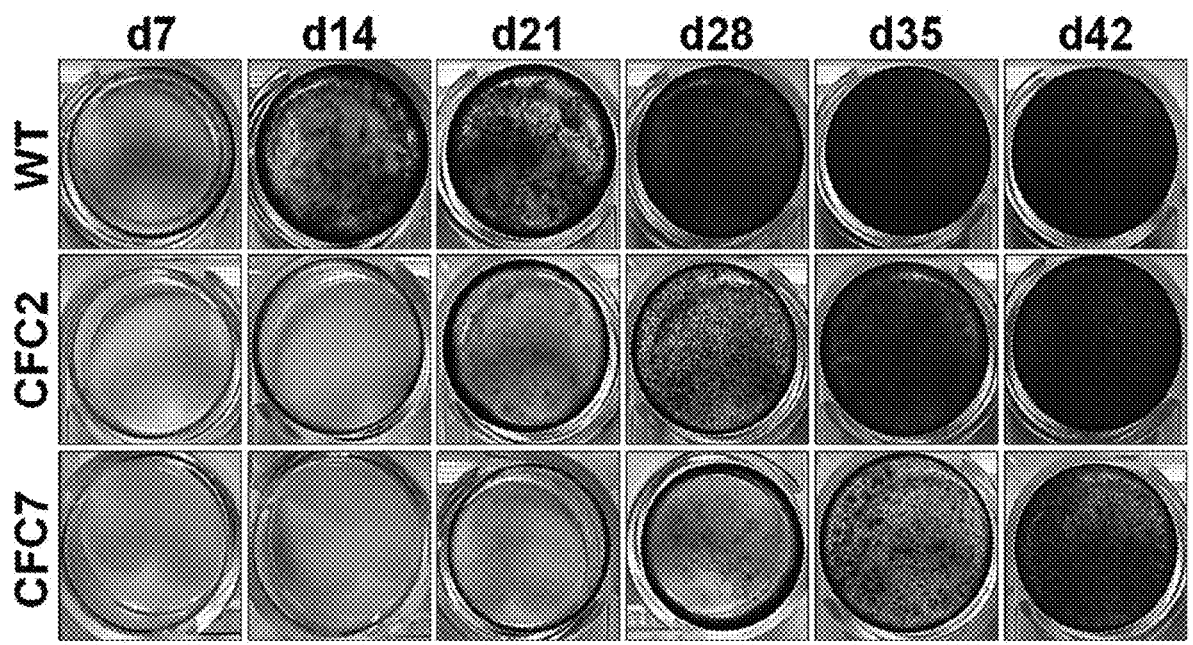

[Figure 8]
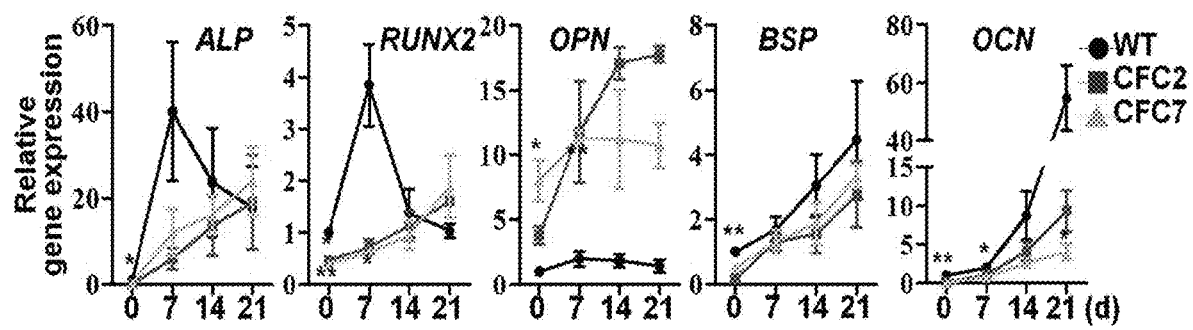

[Figure 9]
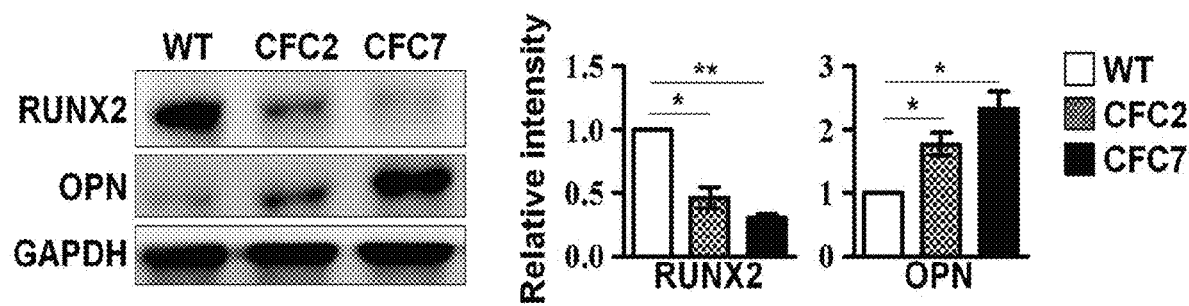

[Figure 10]
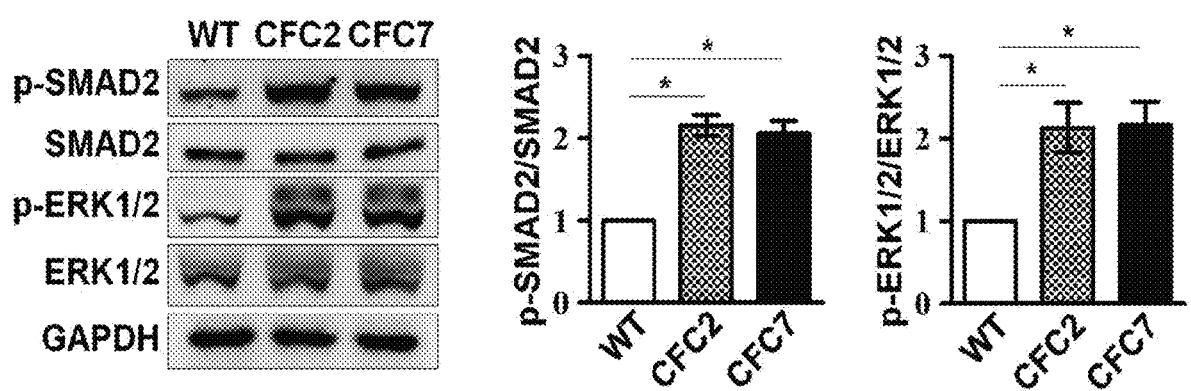

[Figure 11]
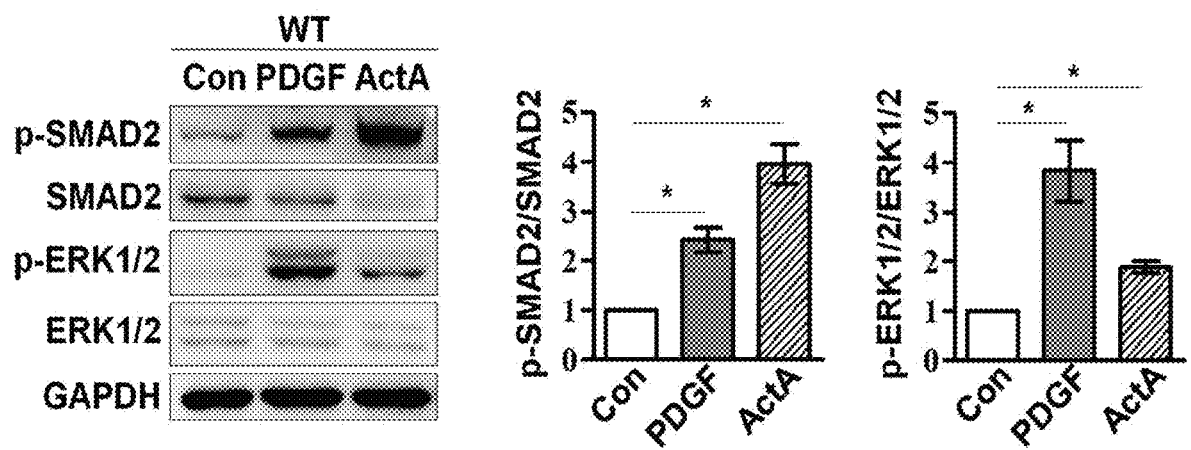

[Figure 12]
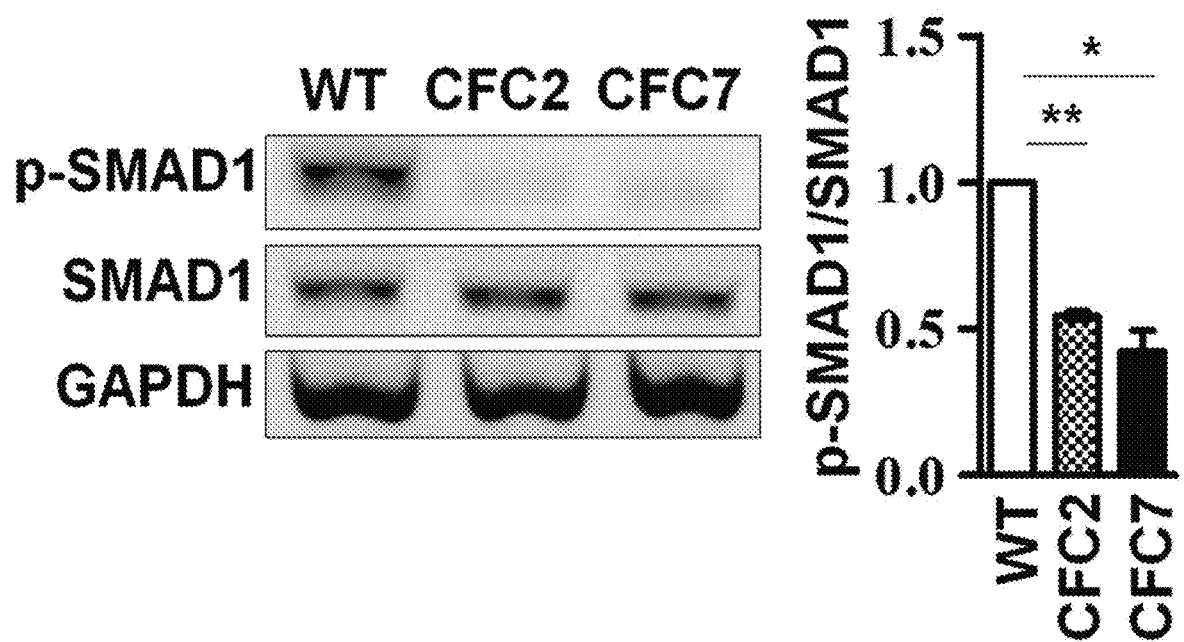

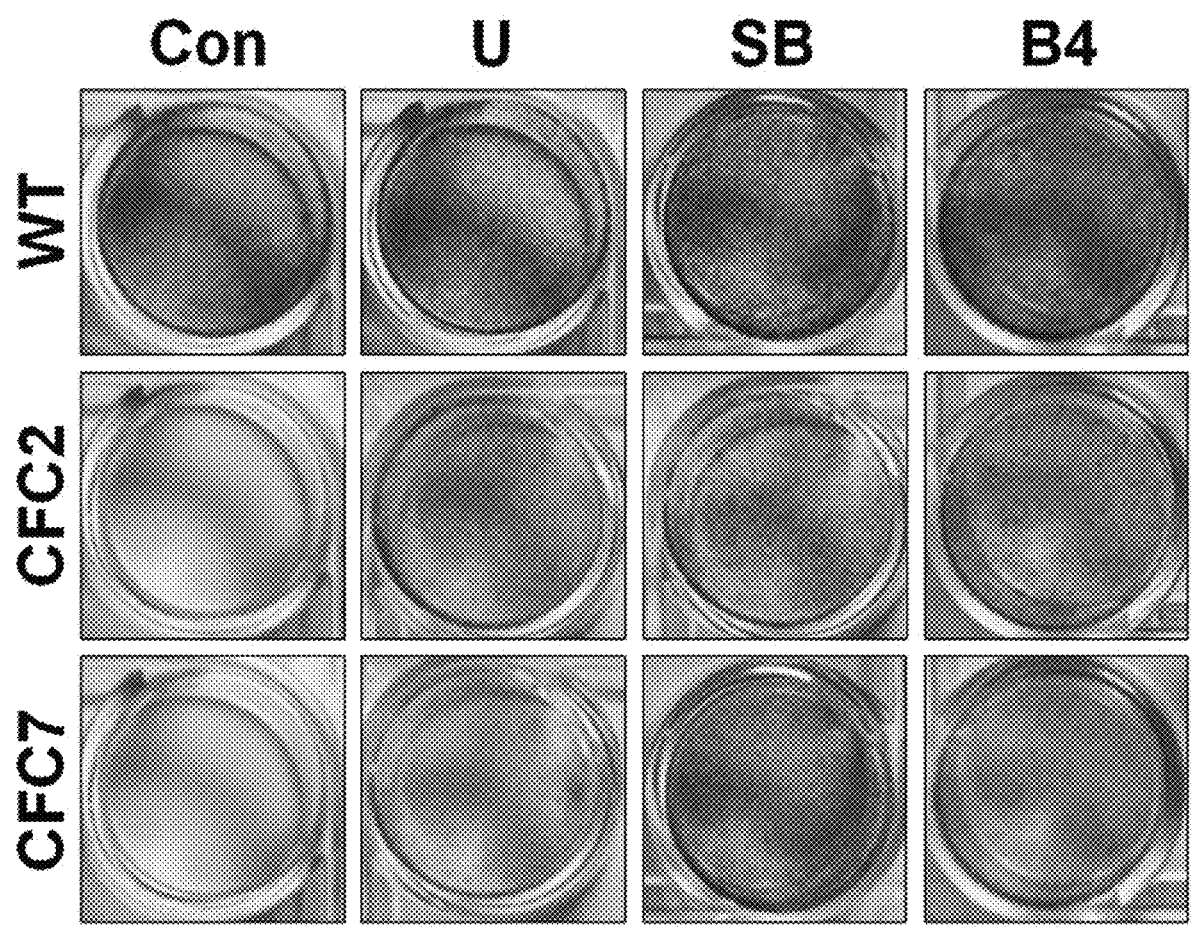
[Figure 13]

[Figure 14]
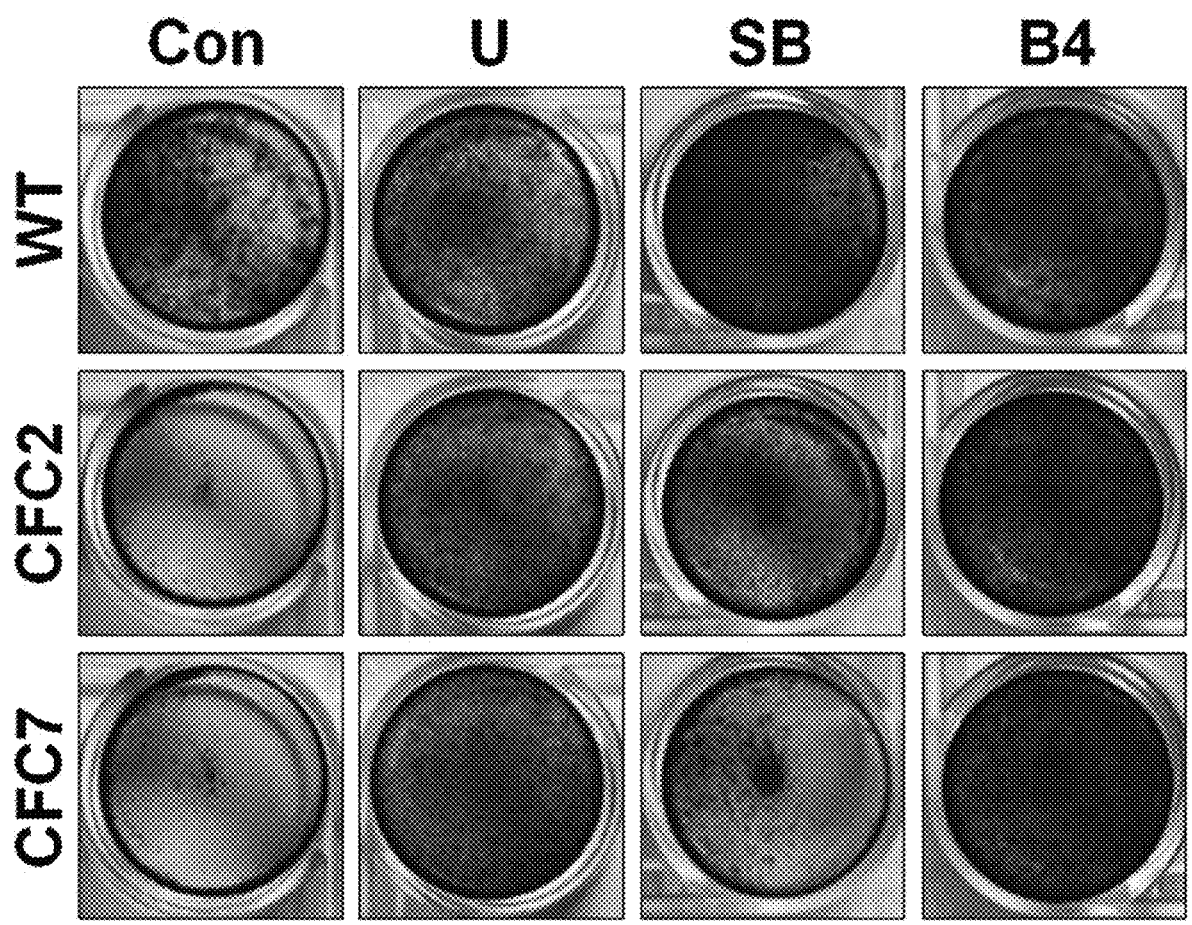

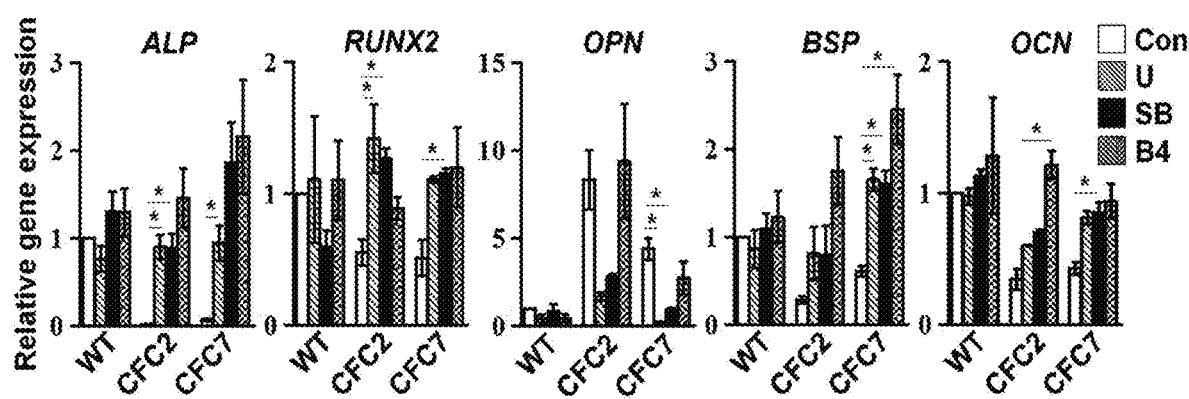
[Figure 15]

SEQUENCE LISTING

```
<160> NUMBER OF SEQ ID NOS: 13

<210> SEQ ID NO 1
<211> LENGTH: 19
<212> TYPE: DNA
<213> ORGANISM: Artificial
<220> FEATURE:
<223> OTHER INFORMATION: GAPDH Forward primer_artificial

<400> SEQUENCE: 1
gaaggtgaag gtcggagtc                                              19

<210> SEQ ID NO 2
<211> LENGTH: 20
<212> TYPE: DNA
<213> ORGANISM: Artificial
<220> FEATURE:
<223> OTHER INFORMATION: GAPDH Reverse primer_artificial

<400> SEQUENCE: 2
gaagatggtg atgggatttc                                             20

<210> SEQ ID NO 3
<211> LENGTH: 20
<212> TYPE: DNA
<213> ORGANISM: Artificial
<220> FEATURE:
<223> OTHER INFORMATION: RUNX2 Forward primer_artificial
```

-continued

<210> SEQ ID NO 3
<211> LENGTH: 20
<212> TYPE: DNA
<213> ORGANISM: Artificial
<220> FEATURE:
<223> OTHER INFORMATION: RUNX2 Forward primer_artificial

<400> SEQUENCE: 3
taggcgcatt tcagatgatg                                         20

<210> SEQ ID NO 4
<211> LENGTH: 20
<212> TYPE: DNA
<213> ORGANISM: Artificial
<220> FEATURE:
<223> OTHER INFORMATION: RUNX2 Reverse primer_artificial

<400> SEQUENCE: 4
gactggcggg gtgtaagtaa                                         20

<210> SEQ ID NO 5
<211> LENGTH: 20
<212> TYPE: DNA
<213> ORGANISM: Artificial
<220> FEATURE:
<223> OTHER INFORMATION: OPN Forward primer_artificial

<400> SEQUENCE: 5
acagccagga ctccattgac                                         20

<210> SEQ ID NO 6
<211> LENGTH: 20
<212> TYPE: DNA
<213> ORGANISM: Artificial
<220> FEATURE:
<223> OTHER INFORMATION: OPN Reverse primer_artificial

<400> SEQUENCE: 6
acactatcac ctcggccatc                                         20

<210> SEQ ID NO 7
<211> LENGTH: 20
<212> TYPE: DNA
<213> ORGANISM: Artificial
<220> FEATURE:
<223> OTHER INFORMATION: OCN Forward primer_artificial

<400> SEQUENCE: 7
ggcagcgagg tagtgaagag                                         20

<210> SEQ ID NO 8
<211> LENGTH: 20
<212> TYPE: DNA
<213> ORGANISM: Artificial
<220> FEATURE:
<223> OTHER INFORMATION: OCN Reverse primer_artificial

<400> SEQUENCE: 8
agcagagcga caccctagac                                         20

<210> SEQ ID NO 9
<211> LENGTH: 20
<212> TYPE: DNA
<213> ORGANISM: Artificial
<220> FEATURE:
<223> OTHER INFORMATION: ALP Forward primer_artificial

<400> SEQUENCE: 9
gtacgagctg aacaggaaca                                         20

<210> SEQ ID NO 10

```
<211> LENGTH: 20
<212> TYPE: DNA
<213> ORGANISM: Artificial
<220> FEATURE:
<223> OTHER INFORMATION: ALP Reverse primer_artificial

<400> SEQUENCE: 10
cttggctttt ccttcatggt                                               20

<210> SEQ ID NO 11
<211> LENGTH: 20
<212> TYPE: DNA
<213> ORGANISM: Artificial
<220> FEATURE:
<223> OTHER INFORMATION: BSP Forward primer_artificial

<400> SEQUENCE: 11
ctcagcattt tgggaatggc                                               20

<210> SEQ ID NO 12
<211> LENGTH: 20
<212> TYPE: DNA
<213> ORGANISM: Artificial
<220> FEATURE:
<223> OTHER INFORMATION: BSP Reverse primer_artificial

<400> SEQUENCE: 12
gtcactactg ccctgaactg                                               20

<210> SEQ ID NO 13
<211> LENGTH: 408
<212> TYPE: PRT
<213> ORGANISM: Homo sapiens

<400> SEQUENCE: 13
```

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn

-continued

```
            195                 200                 205
Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

COMPOSITION FOR PREVENTING OR TREATING CARDIOFACIOCUTANEOUS SYNDROME

CROSS-REFERENCE TO RELATED APPLICATIONS

This application claims priority of Korean Application No. 10-2018-0015574, filed on Feb. 8, 2018.

BACKGROUND OF THE INVENTION

1. Field of the Invention

The present invention relates to a pharmaceutical composition for the prevention or treatment of CFC (cardiofaciocutaneous) syndrome comprising a TGF-β signaling pathway inhibitor or a BMP signaling pathway activator.

2. Description of the Related Art

CFC syndrome is a rare autosomal dominant inherited disease caused by mutation of BRAF gene. BRAF is one of kinases belonging to RAS/MAPK signal transduction system. The mutation of BRAF gene contributes to constant increase of BRAF enzyme activity, and accordingly causes various symptoms which are exemplified by heart malformations, characteristic facial features, skin abnormalities, developmental delays and mental retardation (Niihori, Aoki et al. 2006, Rodriguez-Viciana, Tetsu et al. 2006). In particular, the skeletal system-related symptoms observed in Rasopathy including Noonan syndrome, NF1 and Costello syndrome are also observed in CFC syndrome patients, which are specifically exemplified by bone growth delay, bone density decrease, spine malformation and funnel chest associated with developmental abnormalities and delay of skeletal system (Aoki, Niihori et al. 2008, Abe, Aoki et al. 2012).

Mice with genetic mutations analogous to the CFC syndrome phenotypically revealed vertebra deformity and bone density decrease. However, they do not represent all the skeletal system defects observed in CFC syndrome-patients, and the studies on the pathogenesis mechanism of the above are still insufficient (Inoue, Moriya et al. 2014, Moriya, Inoue et al. 2015). Therefore, studies on the mechanism of CFC syndrome-related skeletal diseases using the samples obtained from CFC patients and screening of therapeutic agents are required.

Stem cells have the differential potential to differentiate into various cells forming each organ, which can be obtained from embryonic, fetal and adult tissues. Stem cells have two competences of a self-renewal capacity characterized by endless proliferation under undifferentiated status and a potential multipotency that induces the cells to differentiate into restricted cells of respective tissues by specific differentiation stimuli. Human pluripotent stem cells (hPSCs) such as human embryonic stem cells (hESCs) and induced pluripotent stem cells (iPSCs) have also the ability to differentiate into various cell types (Carvajal-Vergara, Sevilla et al. 2010). If induced pluripotent stem cells are generated from the somatic cells of a patient, the above-mentioned problems can be solved and at the same time the cells can be used directly as disease model cells because they have the same genetic defects originated from the patient. Therefore, induced pluripotent stem cells can be established from the somatic cells of a specific disease patient and then can be differentiated into desired types of cells, which are useful for the study on pathophysiological mechanism of the disease. These cells are also useful for establishing a platform to screen drug candidates in a large scale, suggesting that the cells can be effectively used in real screening or in predicting and evaluating drug toxicity (Huebsch, Loskill et al. 2016, Sirenko, Hancock et al. 2016).

The present inventors constructed induced pluripotent stem cells from fibroblasts of CFC syndrome patients and investigated the development mechanism of skeletal system related symptoms observed in CFC syndrome-patients. As results, when the induced pluripotent stem cells derived from CFC syndrome patients were induced to differentiate into osteoblasts through mesenchymal stem cells, the differentiation into osteoblasts was inhibited, as compared with the normal control. Based on these results, the present inventors confirmed that the differentiation ability was improved by the treatment of SB-431542, the inhibitor of p-SMAD2. In addition, the present inventors constructed a large scale drug candidates screening platform for measuring ALP (Alkaline Phosphatase) enzyme activity in osteoblasts, with which the present inventors confirmed that a compound that can increase ALP enzyme activity in osteoblasts was successfully screened, leading to the completion of the present invention.

SUMMARY OF THE INVENTION

It is an object of the present invention to provide a pharmaceutical composition for the prevention or treatment of CFC (cardiofaciocutaneous) syndrome. Pharmaceutical compositions comprise one or more TGF-β signaling pathway inhibitors selected from the group consisting of SB-431542, LY2109761, LY2157299, LY-364947, SD-208 and Ki26894 as an active ingredient.

It is another object of the present invention to provide a pharmaceutical composition for the prevention or treatment of CFC (cardiofaciocutaneous) syndrome. The pharmaceutical composition comprises BMP4 (human bone morphogenic protein 4) protein, the BMP signaling pathway activator, as an active ingredient.

To achieve the above objects, the present invention provides a pharmaceutical composition for the prevention or treatment of CFC (cardiofaciocutaneous) syndrome comprising one or more TGF-β signaling pathway inhibitors selected from the group consisting of SB-431542, LY2109761, LY2157299, LY-364947, SD-208 and Ki26894 as an active ingredient.

The present invention also provides a health functional food for the prevention or improvement of CFC (cardiofaciocutaneous) syndrome comprising one or more TGF-β signaling pathway inhibitors selected from the group consisting of SB-431542, LY2109761, LY2157299, LY-364947, SD-208 and Ki26894 as an active ingredient.

The present invention also provides a pharmaceutical composition for the prevention or treatment of CFC (cardiofaciocutaneous) syndrome comprising BMP4 (human bone morphogenic protein 4) protein, the BMP signaling pathway activator, a polynucleotide encoding the BMP4 protein or a vector comprising the polynucleotide above as an active ingredient.

The present invention also provides a health functional food for the prevention or improvement of CFC (cardiofaciocutaneous) syndrome comprising BMP4 (human bone morphogenic protein 4) protein, the BMP signaling pathway activator, a polynucleotide encoding the BMP4 protein or a vector comprising the polynucleotide above as an active ingredient.

The present invention also provides a method for screening drug candidates for treating CFC syndrome, which comprises the following steps:

i) treating a test compound or a composition to the osteoblasts differentiated from iPSCs derived from CFC syndrome patients in vitro;

ii) analyzing the ALP enzyme activity or degree of bone mineral deposition in the osteoblasts of step i); and iii) selecting a test compound or a composition that increased the ALP enzyme activity or degree of bone mineral deposition, compared with the non-treated control group.

Advantageous Effect

The treatment of SB-431542 or BMP4 was confirmed to increase the ALP activity and bone mineral deposition in the osteoblasts differentiated from the induced pluripotent stem cells derived from CFC syndrome patients. Thus, the TGF-β signaling pathway inhibitor containing SB-431542 or the BMP signaling pathway activator containing BMP4 can be effectively used for the prevention or treatment of CFC syndrome.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The application of the preferred embodiments of the present invention is best understood with reference to the accompanying drawings, wherein:

FIG. 1 is a set of photographs illustrating the morphology of the embryonic body (EB) differentiated from the induced pluripotent stem cells derived from CFC syndrome patients (CFC-iPSCs).

WT: induced pluripotent stem cells derived from wild-type; and

CFC2 and CFC7: two induced pluripotent stem cell lines derived from the same CFC syndrome patient.

FIG. 2 is a set of photographs illustrating the morphology of the mesenchymal stem cells (MSCs) differentiated from CFC-iPSCs.

FIG. 3 is a set of graphs illustrating the results of FACS (fluorescence activated cell sorter) presenting the expressions of the positive surface marker and the negative surface marker in MSCs differentiated from CFC-iPSCs.

FIG. 4 is a set of photographs illustrating that the MSCs differentiated from CFC-iPSCs (CFC-MSCs) were differentiated further into chondrocytes and adipocytes, which were stained respectively with alcian blue and oil red O.

FIG. 5 is a set of photographs and a graph illustrating the expression of ERK and p-ERK in CFC-MSCs.

FIG. 6 is a set of graphs illustrating the ALP activity in the osteoblasts differentiated from CFC-MSCs (D # is the date after the differentiation).

FIG. 7 is a set of photographs illustrating the degree of calcium deposition in the osteoblasts differentiated from CFC-MSCs, confirmed by alizarin red S staining.

FIG. 8 is a set of graphs illustrating the results of real-time PCR performed to investigate the mRNA expression levels of ALP, RUNX2, BSP, OCN and OPN, the osteoblast marker genes, in the osteoblasts differentiated from CFC-MSCs.

FIG. 9 is a set of photographs and graphs illustrating the protein expression levels of RUNX2 and OPN, the osteoblast marker proteins, in the osteoblasts differentiated from CFC-MSCs.

FIG. 10 is a set of photographs and graphs illustrating the protein expression levels of ERK/p-ERK and SMAD2/p-SMAD2 in the osteoblasts differentiated from CFC-MSCs.

FIG. 11 is a set of photographs and graphs illustrating the protein expression levels of ERK/p-ERK and SMAD2/p-SMAD2 in the osteoblasts differentiated from WT-MSCs (MSCs differentiated from iPSCs derived from wild-type) and treated with PFGF or Activin A (ActA).

FIG. 12 is a set of photographs and a graph illustrating the protein expression level of SMAD1/p-SMAD1 in the osteoblasts differentiated from CFC-MSCs.

FIG. 13 is a set of photographs illustrating the ALP activity in the osteoblasts differentiated from CFC-MSCs and treated with U0126, SB-431542 and BMP4 protein (recombinant human bone morphogenic protein).

U: U0126, SB: SB-431542, B4: BMP4 protein

FIG. 14 is a set of photographs illustrating the degree of bone mineral deposition in the osteoblasts differentiated from CFC-MSCs and treated with U0126, SB-431542 and BMP4 protein (recombinant human bone morphogenic protein).

U: U0126, SB: SB-431542, B4: BMP4 protein

FIG. 15 is a set of graphs illustrating the results of real-time PCR performed to investigate the mRNA expression levels of ALP, RUNX2, BSP, OCN and OPN, the osteoblast marker genes, in the osteoblasts differentiated from CFC-MSCs and treated with U0126, SB-431542 and BMP4 protein (recombinant human bone morphogenic protein).

U: U0126, SB: SB-431542, B4: BMP4 protein

DESCRIPTION OF THE PREFERRED EMBODIMENTS

Hereinafter, the present invention is described in detail.

The present invention provides a pharmaceutical composition for the prevention or treatment of CFC (cardiofaciocutaneous) syndrome comprising one or more TGF-β signaling pathway inhibitors selected from the group consisting of SB-431542, LY2109761, LY2157299, LY-364947, SD-208 and Ki26894 as an active ingredient.

The said "TGF (transforming growth factor) beta signaling pathway inhibitor" indicates a material that can inhibit the signal transduction mediated by TGF-β. The said TGF-β is a protein that regulates various physiological processes in vivo such as cell proliferation, cell differentiation, apoptosis, cell migration, ECM production, angiogenesis, development, etc.

The TGF-β signaling pathway inhibitor above can be SB-431542, LY2109761, LY2157299, LY-364947, SD-208 or Ki26894, but not always limited thereto and any inhibitor that can inhibit the signal transduction mediated by TGF can be included. In this invention, SB431542 was used as the TGF beta signaling pathway inhibitor, which had the structure of the following formula 1.

[Formula 1]

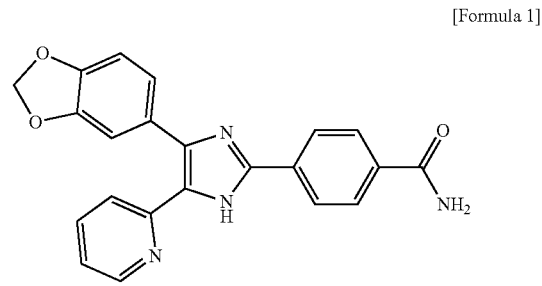 [SMILES: NC(=O)c1ccc(-c2nc(-c3ccc4c(c3)OCO4)c(-c3ccccn3)[nH]2)cc1]

LY2109761 can be the compound represented by formula 2 below, LY2157299 can be the compound represented by formula 3 below, LY-364947 can be the compound represented by formula 4 and SD-208 can be the compound represented by formula 5 below.

[Formula 2]

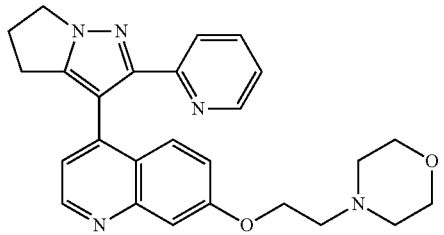

[Formula 3]

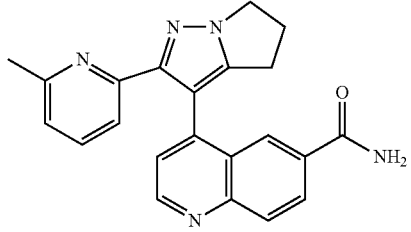

[Formula 4]

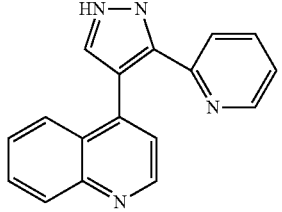

[Formula 5]

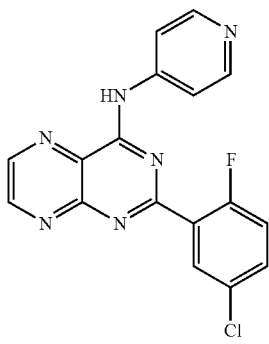

The TGF-β signaling pathway inhibitor above can inhibit the activity of p-SMAD2 in the osteoblasts derived from CFC syndrome patients.

The TGF-β signaling pathway inhibitor above can increase the ALP enzyme activity or bone mineral deposition in the osteoblasts derived from CFC syndrome patients.

The present invention also provides a pharmaceutical composition for the prevention or treatment of CFC (cardiofaciocutaneous) syndrome comprising BMP4 (human bone morphogenic protein 4) protein, a polynucleotide encoding the BMP4 protein or a vector comprising the polynucleotide above as an active ingredient.

The said "BMP (bone morphogenic protein) signaling pathway activator" indicates a material that activates the signal transduction mediated by BMP. BMP is a protein that is directly involved in bone formation in vivo, which plays a crucial role in osteoblast differentiation by promoting differentiation and maturation of osteoblasts.

The BMP signaling pathway activator above can be a BMP4 protein, but is not limited thereto, as long as it is a substance capable of activating BMP signal transduction. In this invention, a BMP4 protein, which is a BMP signaling pathway activator, was used, and at that time the BMP4 protein was consisting of the amino acid sequence represented by SEQ. ID. NO: 13.

The BMP4 protein above can include not only a wild type protein having an activity of activating BMP signaling pathway but also a fragment of the wile type protein or a functional homologue having at least 90% amino acid homology and an activity of activating BMP4 signaling pathway.

Herein, the homology refers to a degree similar to the amino acid sequence of a wild-type protein. The BMP4 protein of the present invention has at least 70%, preferably at least 90%, more preferably at least 90% 95% or more identical amino acid sequence. Herein, the homology is defined by a similarity to the amino acid sequence of the wile type protein. In this invention, the BMP4 protein of the present invention has a homology of at least 70% to the amino acid sequence of the wile type protein represented by SEQ. ID. NO: 13, more preferably has at least 90% and most preferably at least 95% homology to the amino acid sequence of the wile type protein.

The BMP4 protein can include an amino acid sequence variant thereof as long as it retains the activity of activating BMP signaling pathway. Herein, the variant indicates a protein that has a different amino acid sequence from the natural amino acid sequence resulted from deletion, insertion, non-conservative or conservative substitution or a combination thereof.

A polynucleotide encoding the BMP4 protein can be any polynucleotide that can encode the BMP4 protein and has an activity of activating BMP signaling pathway.

A vector containing the polynucleotide encoding the BMP4 protein can be preferably a linear DNA expressed in human or animal cells, a plasmid vector, a vector containing a virus expression vector, or a recombinant virus vector including a recombinant retrovirus vector, a recombinant adenovirus vector, a recombinant adeno-associated virus (AAV) vector, a recombinant herpes simplex virus vector or a recombinant lentivirus vector, but not always limited thereto.

The BMP4 protein above can increase the expression of p-SMAD1 in the osteoblasts derived from CFC syndrome patients.

The BMP4 protein above can increase the ALP enzyme activity or bone mineral deposition in the osteoblasts derived from CFC syndrome patients.

The pharmaceutical composition of the present invention can include, in addition to the active ingredient, one or more effective ingredients having the same or similar function to the active ingredient. The composition of the present invention can also include carriers, diluents, excipients, or a combination of at least two of those, which are commonly used in biological products. The pharmaceutically acceptable carrier can be any carrier that is able to deliver the composition of the present invention in the living body without limitation, which is exemplified by the compounds described in Merck Index, 13th ed., Merck & Co. Inc., such as saline, sterilized water, Ringer's solution, buffered saline, dextrose solution, maltodextrin solution, glycerol, ethanol, or a mixture comprising one or more of those components.

If necessary, a general additive such as antioxidant, buffer, and bacteriostatic agent can be additionally added.

The composition of the present invention can be prepared by mixing with generally used diluents or excipients such as fillers, extenders, binders, wetting agents, disintegrating agents and surfactants. The composition of the present invention can be prepared for oral or parenteral administration.

Solid formulations for oral administration are tablets, pills, powders, granules, capsules and troches. These solid formulations are prepared by mixing the composition with one or more suitable excipients such as starch, calcium carbonate, sucrose, lactose, gelatin, etc. Except for the simple excipients, lubricants, for example magnesium stearate, talc, etc, can be added. Liquid formulations for oral administrations are suspensions, solutions, emulsions and syrups, and the above-mentioned formulations can contain various excipients such as wetting agents, sweeteners, aromatics and preservatives. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc.

The composition of the present invention can be administered orally or parenterally in accordance with the desired method, and the parenteral administration can be performed by external application, intraperitoneal injection, intra-rectal injection, subcutaneous injection, intravenous injection, intramuscular injection or intrathoracic injection.

The composition of the present invention is administered in a pharmaceutically effective dose. The effective dose can be determined according to disease type, severity, activity of the drug, sensitivity to the drug, time of administration, administration pathway and excretion rate, treatment duration, and the drug used simultaneously. The composition of the present invention can be administered alone or in combination with other therapeutic agents. When the composition is administered in combination with other drugs, the administration can be sequential or simultaneous.

The complication of the present invention can be administered alone or together with surgical operation, radiotherapy, hormone therapy, chemo-therapy and biological regulators.

The present invention also provides a health functional food for the prevention or improvement of CFC syndrome (cardiofaciocutaneous syndrome) comprising one or more TGF-β signaling pathway inhibitors selected from the group consisting of SB-431542, LY2109761, LY2157299, LY-364947, SD-208 and Ki26894 as an active ingredient.

The present invention also provides a health functional food for the prevention or improvement of CFC syndrome (cardiofaciocutaneous syndrome) comprising BMP4 (human bone morphogenic protein 4) protein, a polynucleotide encoding the BMP4 protein or a vector comprising the polynucleotide above as an active ingredient.

The term "improvement" used above indicates any action that is taken to relieve the symptoms in those who might have or has CFC syndrome or the action that is beneficiary for the above.

The content of the TGF-β signaling pathway inhibitor or BMP4 protein, which is the active ingredient added to the health functional food of the present invention, can be determined according to the purpose of use. In general, the content can be 0.001 to 0.01 weight part by the total weight of the health functional food.

In addition, there is no particular limitation on the form and the kind of the health functional food herein. The form of the health functional food to which the active ingredient above can be added is a tablet, a capsule, a powder, a granule, a liquid or a pill.

The health functional food of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and *stevia* extract, and synthetic sweetening agents such as saccharin and aspartame can be included as a sweetening agent.

In addition to the ingredients mentioned above, the health functional food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, or alcohols. All the mentioned ingredients can be added singly or together. The mixing ratio of those ingredients does not matter in fact, but in general, each can be added by 001 to 0.1 weight part per 100 weight part of the TGF-β signaling pathway inhibitor or BMP4 protein of the present invention.

In a preferred embodiment of the present invention, the present inventors produced iPSCs (induced pluripotent stem cells) from the fibroblasts of CFC syndrome patients and then investigated the outbreak mechanism of skeletal system related symptoms observed in CFC syndrome patients by using the prepared iPSCs above. As a result, it was confirmed that when CFC syndrome patient derived iPSCs (induced pluripotent stem cells) were differentiated into osteoblasts through the mesenchymal stem cell stage, the differentiation into osteoblasts was inhibited, compared with the normal control group (FIG. 6 to FIG. 10). It was also confirmed that the treatment of SB-431542, a compound that inhibits p-SMAD2, or the treatment of BMP4, a protein that inhibits p-SMAD1, was efficient in improving the differentiation ability (FIG. 13 to FIG. 15). Therefore, the TGF-β signaling inhibitor containing SB-431542 or the BMP signaling pathway activator containing BMP4 protein can be effectively used for a pharmaceutical composition for the prevention or treatment of CFC syndrome and for a health functional food for the prevention or improvement of CFC syndrome.

The present invention also provides a method for screening drug candidates for treating CFC syndrome, which comprises the following steps:

i) treating a test compound or a composition to the osteoblasts differentiated from iPSCs derived from CFC syndrome patients in vitro;

ii) analyzing the ALP enzyme activity or degree of bone mineral deposition in the osteoblasts of step i); and iii) selecting a test compound or a composition that increased the ALP enzyme activity or degree of bone mineral deposition, compared with the non-treated control group.

The present invention also provides a method for screening drug candidates for treating CFC syndrome, which comprises the following steps:

i) treating a test compound or a composition to the osteoblasts differentiated from iPSCs derived from CFC syndrome patients in vitro;

ii) analyzing the expression of one or more osteoblast marker genes selected from the group consisting of ALP (alkaline phosphatase), RUNX2 (runt-related transcription factor 2), BSP (bone sialoprotein), OCN (osteocalcin) and OPN (osteopontin) in the osteoblasts of step i) above; and iii) selecting a test compound or a composition that was able to decrease the expression of ALP, RUNX2, BSP or OCN gene or to increase the expression of OPN gene, compared with the non-treated control group.

The differentiation into osteoblasts in step i) above can be achieved by spontaneous differentiation or by direct induction of differentiation induced by adding a differentiation inducing agent, and the differentiation is preferably achieved through mesenchymal stem cells, but not always limited thereto.

In a preferred embodiment of the present invention, the present inventors produced iPSCs (induced pluripotent stem cells) from the fibroblasts of CFC syndrome patients and then investigated the outbreak mechanism of skeletal system related symptoms observed in CFC syndrome patients by using the prepared iPSCs above. As a result, it was confirmed that when CFC syndrome patient originated iPSCs (induced pluripotent stem cells) were differentiated into osteoblasts through the mesenchymal stem cell stage, the ALP enzyme activity or bone mineral deposition was reduced, compared with the normal control group osteoblasts, and the abnormal expression pattern of the marker gene was observed. Therefore, the osteoblasts differentiated from the CFC syndrome patient originated iPSCs (induced pluripotent stem cells) can be effectively used for a method for screening drug candidates for treating CFC syndrome.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Experimental Example 1: Induction of Mesenchymal Stem Cells (MSCs) from Induced Pluripotent Stem Cells (iPSCs) Derived from CFC Syndrome Patients <1-1> Selection by Clinical Symptoms of CFC Patients To screen the molecular mechanism of skeletal system related symptoms observed in CFC patients and to construct a cell model for the potential drug screening, CFC patients who display typical CFC syndrome symptoms and skeletal system related symptoms such as growth delay, bone density decrease, etc, were selected (Table 1).

TABLE 1

Clinical symptoms of CFC syndrome patients

Overall Symptoms

| Gender Age | Cardiac disorder | Facial malformation | Neck anomaly | Cutaneous anomaly | Short stature | Chest deformity | Mental retardation |
|---|---|---|---|---|---|---|---|
| Male 5.5 year | ○ | hypertelorism, low-set ear, epicanthal folds, downslanting palpebral fissure, macrocephalic | short neck, webbed neck | sparse hair | ○ | pectus excavatum | ○ |

Skeletal System Related Symptoms

| Age | Height | | Weight | | IGF1 | | IGFBP3 | |
|---|---|---|---|---|---|---|---|---|
| year | cm | SD score | kg | SD score | ng/ml | SD score | ng/ml | SD score |
| 5.5 | 99.7 | −2.8 | 17 | −1.3 | 74 | −0.8 | 1630 | −9.3 |
| 6.5 | 107.6 | −2.2 | 19 | −1.2 | 157 | −0.4 | 1854 | −2.7 |
| 7.5 | 113 | −2.2 | 21 | −1.2 | 167 | −0.5 | 2817 | −1.8 |
| 8.5 | 121 | −1.5 | 23 | −1.2 | 404 | 1.9 | 2710 | −2.0 |
| 9.5 | 126.4 | −1.4 | 25.6 | −1.1 | 325 | 0.7 | 2730 | −2.8 |

Bone Density

| Age | Spine AP (L1-L4) | | Femur (Neck) | | Femur (Troch) | | Femur (Whole) | |
|---|---|---|---|---|---|---|---|---|
| year | g/cm$^2$ | SD score | g/cm$^2$ | SD score | g/cm$^2$ | SD score | g/cm$^2$ | SD score |
| 10.5 | 0.588 | −1.6 | 0.698 | −1.4 | 0.540 | −1.5 | 0.646 | −1.7 |

SD is a standard score, which is calculated by the following formula, wherein a negative value indicates that the value is lower than the average, and a larger absolute value means a larger difference from the average value;

$SD$=(patient's value−total mean value)/standard deviation.

There is no Korean standard for bone mineral density in children. A standard score of −1.0 to −2.5 according to USA standard is defined as osteopenia.

<1-2> Separation of Somatic Cells from CFC Patients and Production of iPSCs

After passing the examination of Institutional Review Boards of the hospital, the skin tissue biopsy was performed by the punch biopsy method after local anesthesia with the consent of the CFC patients selected in Experimental Example <1-1> and their legal representative to obtain dermal tissues from CFC patients. Fibroblasts were isolated from the obtained dermal tissues and cultured in Dulbecco's modified Eagle's medium (DMEM; GIBCO, USA) supplemented with 10% fetal bovine serum (FBS; GIBCO, USA), 0.05 mg/mℓ ascorbic acid, 0.3 mg/mℓ L-glutamine (GIBCO, USA), 3.7 mg/mℓ sodium bicarbonate (NaHCO$_3$) and 100 U/mℓ penicillin (GIBCO, USA). Upon completion of the culture, 100μℓ of the cell supernatant was inoculated on a tissue culture plate, and the condition of the culture plate was maintained at 37° C. under 5% carbon dioxide condition for 3 hours. Then, 2 mℓ of culture medium was added thereto, followed by cell culture for 1 week. As a result, fibroblasts were obtained. Then, iPSCs were produced from those CFC patient originated fibroblasts (CFC-iPSCs) by using the ectopic expression method (Takahashi, K et al, Cell 131(5): 861-872, 2007) with the pluripotent markers well known to those in the art such as OCT4, SOX2, KLF4 and C-MYC.

<1-3> Induction of Differentiation of CFC-iPSCs into MSCs (Mesenchymal Stem Cells)

The present inventors investigated whether or not the skeletal system related defects shown in CFC syndrome patients were related to the function of osteoblasts. To do so, the differentiation of CFC-iPSCs was induced and the present inventors investigated whether or not the differentiation of CFC-iPSCs into mesenchymal stem cells (MSCs), the intermediate stage of the differentiation of CFC-iPSCs into osteoblasts, was normally occurred in order to examine the CFC-iPSC differentiation mechanism.

Referring to the protocol proposed in the previous paper 'Mahmood, Harkness et al. 2010', wild type originated iPSC (control) and CFC syndrome patient originated iPSC were induced to be differentiated in vitro for almost 30 days. The iPSCs derived from wild type (WT) individuals and the iPSCs derived from CFC syndrome patients were induced to be differentiated in vitro for about 30 days by referring to the protocol proposed in a previous paper (Mahmood, Harkness et al. 2010). Particularly, CFC-iPSC colony was divided into 4 to 9 sections (0.5 mm×0.5 mm/each section) by using a tissue chopper provided from Mickle Laboratory Engineering Co. The sections were treated with 10 mg/ml of dispase at 37° C. for 4 minutes and then the sections were detached from the cell culture dish. The separated cell sections were transferred in a Petri dish, followed by culture in EB medium (embryoid body differentiation medium), the Dulbecco's modified Eagle's medium (DMEM/F12) supplemented with 10% serum replacement (SR), 1% penicillin-streptomycin and 1% non-essential amino acids, for a day. After confirming EB (embryoid body) was formed with those cell sections, the EBs were further cultured in EB medium supplemented with 10 μM SB-431542 (SB) for 8 days. Then, the EBs were transferred on a culture dish coated with fibronectin, followed by culture in DMEM/F12 supplemented with 1% B27 supplement, 1% insulin-transferrin-selenium liquid media supplement and 1% chemically defined lipid concentrate for 4 days (as attached on the bottom of the culture dish). The EBs were further cultured in MSC culture medium, the α-minimum essential medium (α-MEM) supplemented with 10% fetal bovine serum (FBS) and 1% penicillin-streptomycin for 18 days. The EBs were washed with phosphate-buffered saline (PBS) once and then treated with 0.25% trypsin-EDTA at 37° C. for 2 minutes, leading to the separation of the EBs from the culture dish. The EBs were transferred in a new culture dish. When cells were grown until the confluency reached 70-80% in MSC medium, they were subcultured and used for experiments or stored as frozen. The un-used EBs were stored as frozen. WT-iPSCs were also induced to be differentiated into WT-MSCs by the same manner as described above. As a result, it was confirmed that the morphology (FIG. 1) of the embryoid body, the intermediate stage of the differentiation from iPSCs to MSCs, and the characteristic morphology (FIG. 2) of the final differentiated MSCs were not significantly different between the wild type derived cells and the CFC syndrome patient derived cells.

<1-4> Expression of Surface Marker of MSC Differentiated from CFC-iPSCs

Surface marker analysis was performed to investigate whether the MSCs differentiated from the CFC-iPSCs of Experimental Example <1-3> exhibited the same characteristics as the MSCs derived from wild type iPSCs.

Particularly, for FACS analysis, the MSCs differentiated in Experimental Example <1-3> were washed with PBS once and then treated with accutase at 37° C. for 5 minutes, leading to the separation of the MSCs from the culture dish. The obtained MSCs were washed once with FACS buffer (PBS supplemented with 0.5% FBS), followed by centrifugation at 4° C. at 300×g for 5 minutes. The supernatant was discarded and the submerged cells were resuspended in FACS buffer, followed by filtering with a cell strainer of 40 μm pore size. The filtered cells were washed twice again with FASC buffer, followed by centrifugation at 4° C. at 300×g for 5 minutes. The positive surface markers CD44, CD73, CD90, CD105 and the negative surface markers CD34, CD45, and HLA-DR antibodies were added to the cells resuspended in FACS buffer, followed by reaction at 4° C. for 20 minutes in a dark room. The information on the antibodies used herein is shown in Table 2. The cells reacted with the antibody were washed twice with FACS buffer and fixed with 10% formalin solution at room temperature for 10 minutes. The fixed samples were loaded in a FACS Calibur flow cytometer machine (BD biosciences), followed by reading at least 5,000 cell surface markers. The expression level of the surface markers in each sample was analyzed by using FlowJo program.

TABLE 2

| Information on the antibodies used in FACS | | | | |
|---|---|---|---|---|
| Antibody | Species | Fluorescence | Conc. Co. | Cat. No. |
| CD73 | mouse | PE | 1:100 eBioscience | 12-0739-42 |
| CD90 | mouse | APC | 1:100 eBioscience | 17-0909-42 |
| CD105 | mouse | APC | 1:100 eBioscience | 17-1057-42 |
| CD34 | mouse | APC | 1:100 eBioscience | 17-0349-42 |
| CD45 | mouse | FITC | 1:100 eBioscience | 11-9459-42 |
| HLA-DR | mouse | APC | 1:100 R&D systems | FAB4869A |
| PE-isotype | mouse | PE | 1:100 eBioscience | 12-4714-42 |
| APC-isotype | mouse | APC | 1:100 eBioscience | 17-4714-42 |
| FITC-isotype | mouse | FITC | 1:100 eBioscience | 11-4714-42 |

As a result, it was confirmed that at least 95% of the positive surface markers CD44, CD73, CD90 and CD105 were expressed, while the negative surface markers CD34, CD45 and HLA-DR were not expressed (FIG. 3). The above results indicate that the CFC patient iPSC derived MSCs displayed the same phenotype as the wild type MSCs.

<1-5> Expression of p-ERK in MSCs Differentiated from CFC-iPSCs

Analysis of p-ERK expression was performed by Western blotting in order to investigate whether or not the MSCs differentiated from CFC-iPSCs of Experimental Example <1-3> exhibited the activity of the activation of ERK signaling system in CFC syndrome patients.

The MSCs differentiated in Experimental Example <1-3> were washed with PBS once and then collected by using a scraper. The obtained cells were resuspended in pro-prep protein extraction solution (iNtRON Biotechnology) supplemented with the phosphatase inhibitor mixture comprising 10 mM NaF, 2 mM $Na_3VO_4$ and 1 mM $Na_2P_2O_4$. The cells were lysed by ultrasonication for 3 to 5 times on ice for one second, followed by centrifugation (4° C., 16,100×g, 5 min) to obtain a supernatant containing the cell protein. The protein was quantified by brad-ford assay. The supernatant obtained from the cells was diluted in 60 mM Tris-HCl buffer (pH 6.8) containing 25% glycerol, 2% sodium dodecyl sulfate (SDS), 14.4 mM β-mercaptoethanol and 0.1% bromophenol blue, which was heated for 3 minutes. To separate those proteins having the molecular weight of more than or less than 100 kDa from the heated protein efficiently, the heated protein was separated on 10% and 6% SDS-PAGE gels, respectively. The separated proteins were transferred onto a nitrocellulose membrane, followed by blocking with 4% skim milk (4% skim milk in TBST, TBST; 20 mM Tris [pH 7.5], 145 mM NaCl, 0.05% Tween-20)) or 5% bovine serum albumin (5% bovine serum albumin in TBST). The membrane was treated with the primary antibodies, rabbit originated anti-ERK1/2 antibody (1:2000, Cell signaling Technologies, #9120) and rabbit originated anti-p-ERK1/2 antibody (1:2000, Cell signaling Technologies, #4370), followed by reaction at 4° C. for overnight. On the next day, the membrane was washed with TBST three times. The membrane was treated with the goat anti-rabbit IgG (H+L) secondary antibody (1:5000, HRP conjugate; Thermo scientific) and TBST containing 4% skim milk, followed by reaction at room temperature for one hour. The membrane was washed three times with TBST and treated with an enhanced chemiluminescence (ECL) solution to identify protein bands. The protein bands were quantified by using Image J program. The expression level of each protein was corrected using GAPDH as a control.

As a result, the amount of p-ERK protein was higher in CFC-MSCs than in WT-MSCs, indicating that the activation of ERK signaling system due to the BRAF mutation in CFC syndrome patients was also maintained in the differentiated MSCs. Therefore, CFC-MSCs can be used as a disease cell model for the study of CFC syndrome.

Experimental Example 2: Verification of Differentiation Potency of Mesenchymal Stem Cells (CFC-MSCs) Differentiated from Induced Pluripotent Stem Cells (CFC-iPSCs) Derived from CFC Syndrome Patients <2-1> Differentiation of MSCs Differentiated from CFC-iPSCs into Chondrocytes and Adipocytes The differentiation of chondrocytes and adipocytes from the MSCs differentiated from CFC-iPSCs of Experimental Example <1-3> was induced in order to investigate whether or not the CFC-iPSC derived MSCs were able to maintain the differentiation potency together with the characteristics of MSCs.

To differentiate into chondrocytes, the MSCs were treated with 0.25% trypsin-EDTA at 37° C. for 2 minutes and separated from the culture dish. Then, $1\times10^5$ cells were mixed with 10μℓ of STEMPRO chondrogenesis differentiation medium (Invitrogen), which was loaded in a non-coated round bottom 96 well plate, followed by culture at 37° C. for 1 hour. The same medium was added to the plate (100μℓ /well) and then the plate was cultured continuously. 1 to 2 days later, the aggregated sphere of the cells was observed. The chondrogenesis differentiation medium was changed every 3 days and the cells were suspension-cultured for 21 days. On day 21, the cells were fixed with 10% formalin solution for 10 minutes, and then solidified in 2% agarose gel. The gel was thin-sectioned and the sections were treated with 3% acetic acid for 3 minutes. The sections were treated with alcian blue staining solution at room temperature for 30 minutes. Then, the degree of differentiation into chondrocytes was confirmed. To differentiate into adipocytes, the MSCs were treated with 0.25% trypsin-EDTA at 37° C. for 2 minutes and separated from the culture dish. The cells were spread on a 4-well culture dish at the density of $2.5\times10^4$ cells/$cm^2$, which were cultured in MSC culture medium at 37° C. for 4 days until the cells were full. 4 days later, the medium was replaced with STEMPRO adipogenesis differentiation Medium (Invitrogen). The medium was changed every 3 days and the cells were cultured for 21 days. On day 21, the cells were fixed with 10% formalin solution for 10 minutes, and treated with oil red 0 solution at 60° C. for 15 minutes. Then, the degree of differentiation into adipocytes was confirmed.

As a result, it was confirmed that the wild type individual derived MSCs and the CFC syndrome individual derived MSCs were normally differentiated into chondrocytes or adipocytes.

<2-2> Differentiation of MSCs Differentiated from CFC-iPSCs into Osteoblasts

The MSCs differentiated from CFC-iPSCs of Experimental Example <1-3> were induced to be differentiated into osteoblasts in order to investigate the relation between the function of osteoblasts and the skeletal system related defects shown in CFC syndrome patients.

To differentiate into osteoblasts, the MSCs were treated with 0.25% trypsin-EDTA at 37° C. for 2 minutes and separated from the culture dish. The cells were spread on a 4-well culture dish at the density of $2.5\times10^4$ cells/$cm^2$, which were cultured in MSC culture medium at 37° C. for 3 days until the cells were full. 3 days later, the medium was replaced with STEMPRO osteogenesis differentiation Medium (Invitrogen), and the medium was replaced every three days. The activity of ALP, which is an enzyme essential for the formation of hydroxyapatite, a major component of bone mineral, and an indicator of osteoblast differentiation, was investigated at 7 day intervals by using an ALP kit (Leucocyte Alkaline Phosphatase Kit, Sigma-Aldrich). Particularly, the obtained cells were washed with PBS once, followed by incubation in a fixing solution containing acetone, 37% formaldehyde and citrate solution at room temperature for 30 seconds. The cells were washed with distilled water twice and then stained with distilled water containing sodium nitrate, FRV-alkaline solution and Naphthol As-Bl alkaline solution mixed therein for 1 hour. Then, the degree of color change into blue was observed. In addition, in the course of differentiating MSCs into osteoblasts, alizarin red S staining was performed at 7 day intervals in order to investigate the bone mineral deposition. The cells were washed with PBS once and then fixed in formalin solution at room temperature for 10 minutes. The cells were washed with distilled water three times, followed by staining with alizarin red S solution at room temperature for 20 minutes. The cells were washed with distilled water twice and the degree of color change into red was measured to investigate the calcium ion deposition.

As a result, the ALP activity of CFC-MSCs was lower than that of WT-MSCs at the early differentiation stage and the ALP activity of CFC-MSCs reached to the normal level 4 weeks after, indicating the delayed differentiation phenomenon was confirmed (FIG. 6). In addition, it was observed that the calcium deposition was reduced in the CFC syndrome derived osteoblasts than the WT derived osteoblasts (FIG. 7). These results indicate that the differentiation and maturation of the MSCs derived from CFC syndrome patients into osteoblasts were impaired or retarded.

Experimental Example 3: Molecular Mechanism of Impairment of Differentiation and Maturation of CFC-MSCs into Osteoblasts <3-1> Comparison of Marker Gene Expression Level in Differentiation of CFC-MSCs into Osteoblasts To investigate the cause of abnormal differentiation of CFC-MSCs into osteoblasts, the mRNA expression levels of ALP, RUNX2, BSP, OCN and OPN, the osteoblast differentiation related marker genes, were measured during the differentiation into osteoblasts by real-time PCR.

The differentiation of WT-MSCs and CFC-MSCs into osteoblasts was induced by the same manner as described in Experimental Example <2-2>. On day 7, cells were obtained. The obtained cells were suspended in TRIzol (Invitrogen, USA), from which RNA was extracted according to the manufacturer's protocol. First-strand cDNA was synthesized by using Oligo dT primer and M-MLV reverse transcriptase (Enzynomics) with 1 μg of the extracted RNA as a template. Real-time PCR was performed with CFX-Connect real-time detection system (Bio-Rad) using the synthesized cDNA above as a template with the primer sets for the respective genes listed in Table 3 to confirm the relative expression level of each gene in the osteoblasts differentiated from CFC-MSCs (CFC-osteoblasts). To correct the expression level, GAPDH gene was used as a control. ΔCt value of each gene was calculated according to the difference of Ct value of GAPDH and each gene.

The expression level of each gene in the osteoblasts differentiated from WT-MSCs (WT-osteoblasts) was also investigated, which was compared with the expression level of each gene in the osteoblasts differentiated from CFC-MSCs (CFC-osteoblasts). The results were presented by the fold change calculated by $2^{-(S\Delta Ct-C\Delta Ct)}$ (SΔCt: ΔCt value of each gene in CFC-iPS; and CΔCt: ΔCt value of each gene in WT-iPS).

TABLE 3

Primers used for real-time PCR and their sequences

| Gene | Primer | Sequence (5' to 3') | SEQ. ID. NO |
|------|--------|---------------------|-------------|
| GAPDH | GAPDH_F | GAAGGTGAAGGTCGGAGTC | 1 |
|  | GAPDH_R | GAAGATGGTGATGGGATTTC | 2 |
| RUNX2 | RUNX2_F | TAGGCGCATTTCAGATGATG | 3 |
|  | RUNX2_R | GACTGGCGGGGTGTAAGTAA | 4 |
| OPN | OPN_F | ACAGCCAGGACTCCATTGAC | 5 |
|  | OPN_R | ACACTATCACCTCGGCCATC | 6 |

TABLE 3-continued

Primers used for real-time PCR and their sequences

| Gene | Primer | Sequence (5' to 3') | SEQ. ID. NO |
|------|--------|---------------------|-------------|
| OCN | OCN_F | GGCAGCGAGGTAGTGAAGAG | 7 |
|  | OCN_R | AGCAGAGCGACACCCTAGAC | 8 |
| ALP | ALP_F | GTACGAGCTGAACAGGAACA | 9 |
|  | ALP_R | CTTGGCTTTTCCTTCATGGT | 10 |
| BSP | BSP_F | CTCAGCATTTTGGGAATGGC | 11 |
|  | BSP_R | GTCACTACTGCCCTGAACTG | 12 |

As a result, it was confirmed that the expression levels of ALP, RUNX2, BSP and OCN genes in CFC-osteoblasts were lower than those in WT-osteoblasts in general. On the other hand, the expression of OPN gene was higher in CFC-osteoblasts than in WT-osteoblasts (FIG. 8).

<3-2> Comparison of Marker Protein Expression in the Course of Differentiation of CFC-MSCs into Osteoblasts To identify the cause of abnormal differentiation of CFC-MSCs into osteoblasts, the protein expression levels of RUNX2 and OPN, the osteoblast differentiation related marker genes, were measured during the differentiation into osteoblasts by Western blotting.

The differentiation of WT-MSCs and CFC-MSCs into osteoblasts was induced by the same manner as described in Experimental Example <2-2>. On day 7, cells were obtained, followed by Western blotting by the same manner as described in Experimental Example <1-5>. As the primary antibodies, rabbit originated anti-RUNX2 antibody (1:1000, Cell signaling Technologies, #12556) and mouse originated anti-OPN antibody (1:1000, Abcam, ab69498) were treated to the cells. As the secondary antibody to the mouse originated anti-OPN antibody, HRP conjugated goat anti-mouse IgG (H+L) secondary antibody (Santa Cruz) was used.

As a result, the expression of RUNX2 protein was reduced but the expression of OPN protein was increased, which was consistent with the result of Experimental Example <3-1> (FIG. 9). It is known that the decrease of RUNX2 expression has the effect of inhibiting the osteoblast differentiation by suppressing the expressions of other differentiation related genes overall. So, this might also affect the differentiation of CFC-osteoblasts to cause abnormal differentiation and maturation.

<3-3> Expression of p-ERK and p-SMAD2 in the Course of Differentiation of CFC-MSCs into Osteoblasts In relation to the abnormal differentiation of CFC-MSCs into osteoblasts, Western blotting was performed to investigate the activation level of the ERK signaling pathway and the transforming growth factor-beta (TGF-beta) signaling pathway. The activity of TGF-beta signal transduction system can be examined by measuring the expression level of p-SMAD2. It is known to inhibit the maturation of osteoblasts when the pathway is over-activated (Erlebacher and Derynck 1996, Maeda, Hayashi et al. 2004).

The differentiation of WT-MSCs and CFC-MSCs into osteoblasts was induced by the same manner as described in Experimental Example <2-2>. On day 7, cells were obtained, followed by Western blotting by the same manner as described in Experimental Example <1-5>. As the primary antibodies, rabbit originated anti-ERK1/2 antibody (1:1000, Cell signaling Technologies, #9120), rabbit originated anti-p-ERK1/2 antibody (1:1000, Cell signaling Technologies, #4370), rabbit originated anti-SMAD2/3 antibody (1:500, Cell signaling Technologies, #3102) and rabbit originated anti-p-SMAD2 antibody (1:500, Cell signaling Technologies, #3108) were treated to the cells.

As a result, it was confirmed that the p-ERK and p-SMAD2 levels were significantly increased in the osteoblasts differentiated from CFC-MSCs, compared with the osteoblasts differentiated from WT-MSCs (FIG. 10).

<3-4> Correlation Between ERK Signaling Pathway and Transforming Growth Factor-Beta (TGF-Beta) Signaling Pathway in the Course of Differentiation of MSCs into Osteoblasts To investigate the crosstalk between the activated ERK signaling pathway and the TGF-beta signaling pathway in the osteoblasts differentiated from CFC-MSCs, the cells were treated with PDGF (platelet-derived growth factor) or Activin A (50 ng/ml) that can artificially activate each signal transduction system in normal osteoblasts, followed by Western blotting.

Particularly, the differentiation of WT-MSCs into osteoblasts was induced by the same manner as described in Experimental Example <2-2>. On day 1, the cells were treated with PDGF at the concentration of 10 ng/ml or activin A at the concentration of 50 ng/ml. On day 7, cells were obtained, followed by Western blotting by the same manner as described in Experimental Example <1-5>.

As a result, it was observed that the ERK and TGF-beta signaling pathways showed a positive feedback phenomenon when either one of them was activated, thereby increasing the activity of the other. As a result, a positive feedback phenomenon was observed, that is when one of the two signaling pathways, either ERK or TGF-beta signaling pathway, was activated, it can increase the activity of the other (FIG. 11). The above result suggests that an abnormal increase of the TGF-beta signal transduction system in CFC-osteoblasts can be caused by the activation of the ERK signal transduction system by BRAF mutation.

<3-5> Expression of pSMAD1 in the Course of Differentiation of MSCs into Osteoblasts It has been reported that BMP (bone morphogenic protein) signaling pathway plays an essential role in osteoblast differentiation by promoting the differentiation and maturation of osteoblast (Phimphilai, Zhoa et al. 2006). Thus, the present inventors examined the BMP signaling pathway in the osteoblasts differentiated from CFC-MSCs by measuring the expression of p-SMAD1 which is a key indicator of the BMP signal transduction system.

The differentiation of WT-MSCs and CFC-MSCs into osteoblasts was induced by the same manner as described in Experimental Example <2-2>. On day 7, cells were obtained, followed by Western blotting by the same manner as described in Experimental Example <1-5>.

As the primary antibodies, rabbit originated anti-p-SMAD1/5/9 antibody (1:500, Cell signaling Technologies, #13820) and rabbit originated anti-SMAD1 antibody (1:500, Cell signaling Technologies, #9743) were treated to the cells. The level of p-SMAD1 in CFC-osteoblasts, that is, the activity of the BMP signal transduction system, was significantly lower than that in WT-osteoblasts, which was confirmed by Western blotting (FIG. 12).

As a result, the expression of p-SMAD1 was significantly suppressed in the osteoblasts differentiated from CFC-MSCs, suggesting that the BMP signaling pathway was significantly inhibited, compared with the osteoblasts differentiated from WT-MSCs (FIG. 12). The above result was consistent with the result of Experimental Example <2-2>, which was the confirmation of the inhibition of differentiation potency of CFC-MSCs into osteoblasts.

Experimental Example 4: Confirmation of Therapeutic Effect on CFC Syndrome Patients by Regulating ERK Signaling Pathway, TGF-Beta Signaling Pathway and BMP Signaling Pathway <4-1> Increase of ALP Enzyme Activity and Bone Mineral Deposition in CFC-Osteoblasts by Regulating ERK Signaling Pathway, TGF-Beta Signaling Pathway and BMP Signaling Pathway The present inventors investigated whether or not the regulation of ERK signaling pathway, TGF-beta signaling pathway or BMP signaling pathway could recover the suppressed ALP enzyme activity and bone mineral deposition.

Particularly, the differentiation of CFC-MSCs into osteoblasts was induced by the same manner as described in Experimental Example <2-2>. On day 1, the cells were treated with the ERK signaling pathway inhibitor U0126 (Cell Signaling Technology) at the concentration of 5 μM, the TGF-beta signaling pathway inhibitor SB-431542 (SB, Cayman Chemical) at the concentration of 5 μM and the BMP signaling pathway activator, the recombinant protein BMP4 (human bone morphogenic protein 4, R&D systems), at the concentration of 50 ng/ml for 24 hours. ALP enzyme activity was measured on the $7^{th}$ day of the differentiation, and alizarin red S staining was performed on the $14^{th}$ day of the differentiation by the same manner as described in Experimental Example <2-2>. On day 21, von Kossa staining was performed. Particularly, the cells were washed with PBS once, and fixed with formalin solution at room temperature for 10 minutes. The cells were washed with distilled water three times. Then, the cells were incubated with 5% silver nitrate solution at room temperature for 1 hour under ultraviolet light. After washing the cells with distilled water twice, the amount of calcium deposition was evaluated by the degree of darkening.

As a result, the inhibition of the ERK signaling pathway or TGF-beta signaling pathway or the activation of the BMP signaling pathway resulted in the increase of the ALP enzyme activity (FIG. 13) and bone mineral deposition in the osteoblasts differentiated from CFC-MSCs (FIG. 14). That is, the abnormal defects observed in the course of differentiation of CFC-MSCs into osteoblasts could be restored normally by regulating the pathways above.

<4-2> Recovery of CFC-Osteoblast Marker Gene Expression by Regulating ERK Signaling Pathway, TGF-Beta Signaling Pathway and BMP Signaling Pathway By the same manner performed in Experimental Example <4-1>, it was investigated whether or not the decreased marker gene expression in CFC-osteoblasts, confirmed in Experimental Example <3-1>, was able to be recovered to the normal level by the treatment of the ERK signaling pathway, the TGF-beta signaling pathway or the BMP signaling pathway regulating substance.

Particularly, the differentiation of CFC-MSCs into osteoblasts was induced by the same manner as described in Experimental Example <2-2>. On day 1, the cells were treated with the ERK signaling pathway inhibitor U0126 (Cell Signaling Technology) at the concentration of 5 μM, the TGF-beta signaling pathway inhibitor SB-431542 (SB, Cayman Chemical) at the concentration of 5 μM or the BMP signaling pathway activator, the recombinant protein BMP4 (human bone morphogenic protein 4, R&D systems), at the concentration of 50 ng/ml for 24 hours. On the $7^{th}$ day of the differentiation, cells were collected, followed by real-time PCR to investigate the expressions of ALP, RUNX2, OCN, OPN and BSP genes by the same manner as described in Example <3-1> above.

As a result, the gene expression that was changed in CFC-osteoblasts was recovered in the normal direction (FIG. 15). The above result indicates that the defect of CFC-osteoblasts can be recovered by regulating the ERK signaling pathway, the TGF-beta signaling pathway or the BMP signaling pathway, by which the present invention provides a novel molecular biological target and a candidate for the treatment of CFC syndrome patients.

Experimental Example 5: Establishment of Drug Screening Platform Using CFC-MSCs and Osteoblasts Differentiated Therefrom ALP is a very important enzyme playing an essential role in osteoblast differentiation and bone mineral formation. CFC-osteoblasts exhibit lower ALP enzyme activity than WT-osteoblasts. Therefore, it is expected that if a compound that is able to recover the ALP activity in CFC-osteoblasts is found, that compound can be applied to treat osteodystrophy and bone density decrease of CFC-syndrome patients. Therefore, a platform for screening such drugs in a large scale has been established.

<5-1> Establishment of Efficient Mass Induction of CFC-MSCs Derived from CFC-iPSCs into Osteoblasts/Compound Treatment Conditions The cultured MSCs were washed with PBS once, and then treated with 0.25% trypsin-EDTA at 37° C. for 2 minutes and separated from the culture dish. The cells were resuspended in osteoblast culture medium and distributed in a 384 well plate (black, optically clear bottom, tissue culture treated, sterile, greiner) at the density of $5 \times 10^3$ cells/40 μl/well. Labsystems MultiDrop 384 (BECKMAN COULTER) was used to distribute the cells uniformly. 24 hours later, the compound to be used for screening, the positive control and the negative control were treated to each well at a required concentration, followed by further culture for 6 days without changing the medium. Biomek FXp Laboratory Automation Workstation (BEXKMAN COULTER) was used to dilute the compounds to a constant concentration and add them to the 384 well plate.

<5-2> Establishment of Stable Quantitative Analysis Condition of ALP Enzyme Activity in Mass Culture Condition of Differentiated Osteoblasts The cells differentiated after being treated with the compound as shown in Example <5-1> above were washed with PBS (85 μl/well) once on day 7. The cells were treated with 1-step PNPP solution (30 μl/well, Thermo Scientific) at room temperature for 20 minutes. 2 N NaOH (15 μl/well) was additionally treated thereto to terminate the reaction. Absorbance was measured at 405 nm to compare the ALP enzyme activity. In the analysis, the solution was applied to a 384 well plate by using Labsystems MultiDrop 384 (BECKMAN COULTER). The osteoblasts differentiated from WT-MSCs were used as the normal control, the CFC-osteoblasts treated with dimethyl sulfoxide (DMSO) were used as the negative control, and the CFC-osteoblasts treated with 5 μM SB-431542 were used as the positive control. To reduce the edge effect, the edge wells of the 384 well plate were emptied or filled with distilled water. Each well was set by a basal level to correct the absorbance values.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating cardiofaciocutaneous (CFC) syndrome, comprising administering a pharmaceutically effective amount of one or more inhibitors of TGF-β signaling pathway selected from the group consisting of SB-431542, LY2109761, LY2157299, LY-364947, SD-208, and Ki26894.

2. The method for treating CFC syndrome according to claim 1, wherein the one or more inhibitors of TGF-β signaling pathway decreases activity of p-SMAD2 in CFC syndrome patient-originated osteoblasts.

3. The method for treating CFC syndrome according to claim 1, wherein the one or more inhibitors of TGF-β signaling pathway increases ALP enzyme activity or bone mineral deposition in CFC syndrome patient-originated osteoblasts.

* * * * *